United States Patent

Saito et al.

[11] Patent Number: 6,068,599
[45] Date of Patent: May 30, 2000

[54] BLOOD VESSEL PUNCTURING DEVICE USING ULTRASOUND

[75] Inventors: Koetsu Saito, Tokyo; Shuko Tomisawa, Yokohama; Toru Nibuya, Tokyo; Masami Kawabuchi, Yokohama, all of Japan

[73] Assignee: Matsushita Electric Industrial Co., Ltd., Osaka, Japan

[21] Appl. No.: 09/114,184

[22] Filed: Jul. 13, 1998

[30] Foreign Application Priority Data

Jul. 14, 1997 [JP] Japan .................................. 9-188466
Nov. 20, 1997 [JP] Japan .................................. 9-334788

[51] Int. Cl.[7] ...................................................... A61B 8/02
[52] U.S. Cl. .......................................... 600/454; 600/461
[58] Field of Search ..................... 600/461, 462, 600/466, 454; 606/213; 604/53; 128/214 R

[56] References Cited

U.S. PATENT DOCUMENTS

| | | | |
|---|---|---|---|
| 4,324,236 | 4/1982 | Gordon et al. | 128/214 R |
| 4,608,989 | 9/1986 | Drue | 600/461 |
| 4,671,292 | 6/1987 | Matzuk . | |
| 4,904,240 | 2/1990 | Hoover | 604/53 |
| 5,131,394 | 7/1992 | Gehlbach | 600/461 |
| 5,158,088 | 10/1992 | Nelson et al. | 600/461 |
| 5,261,409 | 11/1993 | Dardel . | |
| 5,645,566 | 7/1997 | Brenneman et al. | 606/213 |

FOREIGN PATENT DOCUMENTS

| | | |
|---|---|---|
| 3501355 | 7/1985 | Germany . |
| 4206065 | 9/1993 | Germany . |
| 5-168636 | 7/1993 | Japan . |

OTHER PUBLICATIONS

"Development of the Stand Off Attachment of Linear Probe for Oblique Scanning and Puncture" by T. Imai et al; JSUM Proceedings; Oct.–Nov. 1990.

*Primary Examiner*—Marvin M. Lateef
*Assistant Examiner*—Ali M. Imam
*Attorney, Agent, or Firm*—Pollock, Vande Sande & Amernick

[57] ABSTRACT

A blood vessel puncturing device includes an ultrasound sensor which is brought into close contact with a subject body via an ultrasound propagation medium in the form of gel. The ultrasound sensor transmits and receives an ultrasound wave. The device further includes a processor which processes a signal derived from the ultrasound wave received at the ultrasound sensor so as to display an image of the subject body including a superficial blood vessel. While watching the displayed image, an operator sticks a puncturing needle at an angle of not greater than 30 degrees relative to the subject body along an ultrasound scanning surface of the ultrasound sensor and inserts the tip of the puncturing needle into the blood vessel. It may be arranged that a change in blood flow in the blood vessel is detected based on a Doppler signal or a change in luminance at a designated region on the displayed image is detected, and the detected change is notified in the form of an audible sound so that the operator confirms insertion of the puncturing needle into the blood vessel.

8 Claims, 6 Drawing Sheets

BLOOD VESSEL PUNCTURING DEVICE USING ULTRASOUND

BACKGROUND OF THE INVENTION

1. Field of the Invention

The present invention relates to a blood vessel puncturing device using ultrasound waves and, in particular, to a blood vessel puncturing device which enables easy and accurate insertion of a puncturing needle into a blood vessel of a subject body for blood gathering or medical fluid injection.

2. Description of the Prior Art

Figure 6:
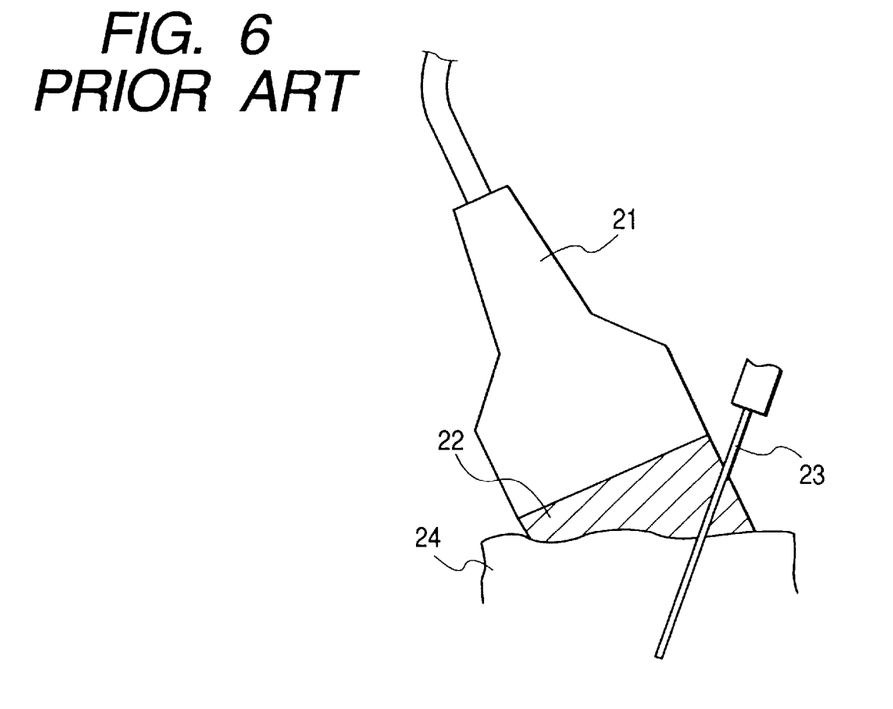
FIG. 6 is a sectional view showing a schematic structure of a conventional blood vessel puncturing device.

FIG. 6 shows a blood vessel puncturing device similar to that described in "Linear Scanning Probe for Superficial Portion" printed in the Japan Ultrasound Medical Institute Lecture Collection 57-300 (October and November, 1990).

In FIG. 6, numeral 21 denotes an ultrasound probe for transmitting and receiving ultrasound waves, 22 a solid attachment, 23 a puncturing needle and 24 a subject body. The solid attachment 22 is provided between the ultrasound probe 21 and the subject body 24, and the puncturing needle 23 is stuck into the subject body 24 via the solid attachment 22.

Figure 7:
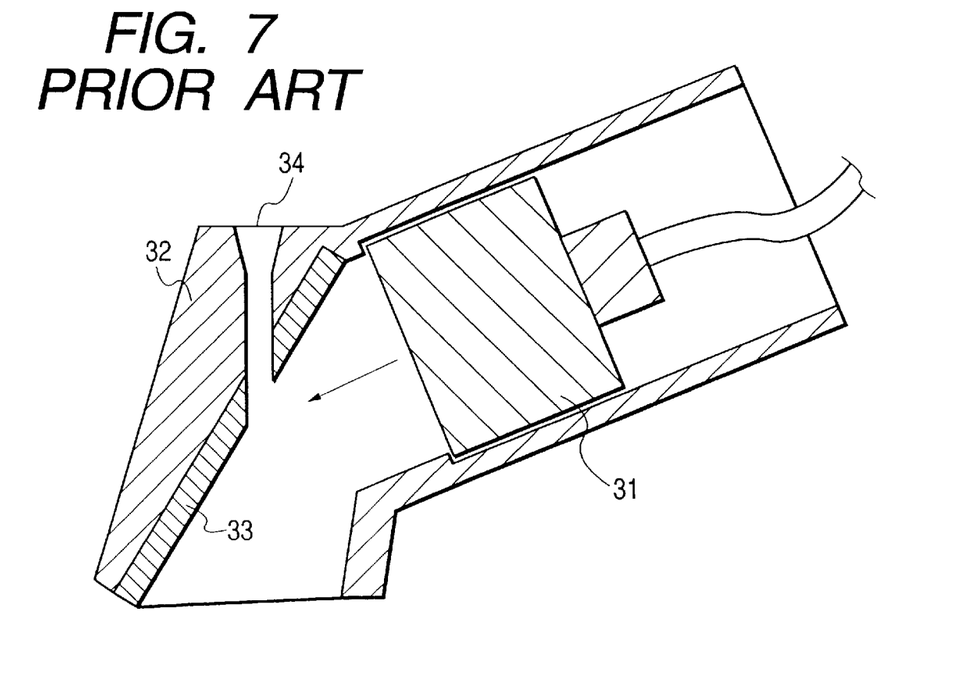
FIG. 7 is a sectional view showing a schematic structure of a conventional blood vessel puncturing device.

On the other hand, FIG. 7 shows a blood vessel puncturing device similar to that described in U.S. Pat. No. 5,261,409 (equivalent to JP-A5-168636).

In FIG. 7, the blood vessel puncturing device comprises an ultrasound probe 31 and a housing 32 which holds a puncturing needle. The ultrasound beam emitted from the ultrasound probe 31 is reflected off a reflector 33 provided in the housing 32 so as to enter a subject body in parallel to a needle holding hole 34 formed through the housing 32 and the reflector 33. Then, the ultrasound waves reflected from the subject body are reflected off the reflector 33 so as to be received at the ultrasound probe 31. A blood vessel is located based on the Doppler effect so that the puncturing needle is inserted into the needle holding hole 34 and stuck into the located blood vessel.

However, in case of the scanning probe shown in FIG. 6, since the solid attachment is used, it is necessary to press the solid attachment onto the surface of the subject body applying a certain force for tightly contacting the solid attachment with the subject body whose surface shape is not constant. This causes deformation of a superficial blood vessel so that the puncturing needle can not be precisely stuck into the blood vessel. Further, since an angle between the puncturing needle and the surface of the subject body is set not less than 45 degrees when sticking the needle into the subject body, it is difficult to stick the needle with accuracy into a blood vessel, particularly a fine blood vessel, extending in parallel to the surface of the subject body.

On the other hand, in case of the blood vessel puncturing device shown in FIG. 7, since no fixing means is provided for the device, it is possible that the device itself moves when sticking the needle into the blood vessel. Further, since the insertion depth of the needle into the subject body can not be known, the needle can not be precisely stuck into the blood vessel.

SUMMARY OF THE INVENTION

Therefore, it is an object of the present invention to provide a blood vessel puncturing device which is essentially free of deformation of a superficial blood vessel of a subject body and makes it possible to easily and precisely stick a puncturing needle into the blood vessel.

According to one aspect of the present invention, there is provided a blood vessel puncturing device comprising an ultrasound sensor for transmitting and receiving an ultrasound wave to and from a subject body; a processor for processing a signal derived from the ultrasound wave received at the ultrasound sensor to display an image of the subject body; an ultrasound propagation medium in the form of gel interposed between the ultrasound sensor and the subject body; and a puncturing needle which is stuck into the subject body at an angle of not greater than 30 degrees relative to the subject body along an ultrasound scanning surface of the ultrasound sensor.

It may be arranged that the ultrasound sensor has a housing provided with a guide member for guiding the puncturing needle so as to be stuck at the angle relative to the subject body.

It may be arranged that an image display monitor is provided near a housing of the ultrasound sensor.

It may be arranged that the ultrasound sensor carries out one of electronic convex-type scanning and electronic sector-type scanning.

According to another aspect of the present invention, there is provided a blood vessel puncturing device comprising an ultrasound sensor for transmitting and receiving an ultrasound Doppler signal: a section for locating a blood vessel based on the ultrasound Doppler signal received at the ultrasound sensor; a section for detecting insertion of a puncturing needle into the blood vessel based on the ultrasound Doppler signal received at the ultrasound sensor; and a section for converting the ultrasound Doppler signal received at the ultrasound sensor into an audible sound.

It may be arranged that the ultrasound sensor is an electronic scanning ultrasound probe.

It may be arranged that the ultrasound sensor further transmits and receives an ultrasound signal, and the blood vessel puncturing device further comprises a section for displaying an image of the blood vessel based on the ultrasound signal received at the ultrasound sensor.

According to another aspect of the present invention, there is provided a blood vessel puncturing device comprising an ultrasound sensor for transmitting and receiving an ultrasound wave to and from a subject body; a section for displaying an image of the subject body based on the ultrasound wave received at the ultrasound sensor; a section for setting a region on the displayed image; a section for detecting a luminance in the region; and a section for outputting a change of the luminance in the form of an audible sound.

BRIEF DESCRIPTION OF THE DRAWINGS

The present invention will be understood more fully from the detailed description given hereinbelow, taken in conjunction with the accompanying drawings.

In the drawings.

DESCRIPTION OF THE PREFERRED EMBODIMENT

Now, preferred embodiments of the present invention will be described hereinbelow with reference to the accompanying drawings.

(First Embodiment)

Figure 1:
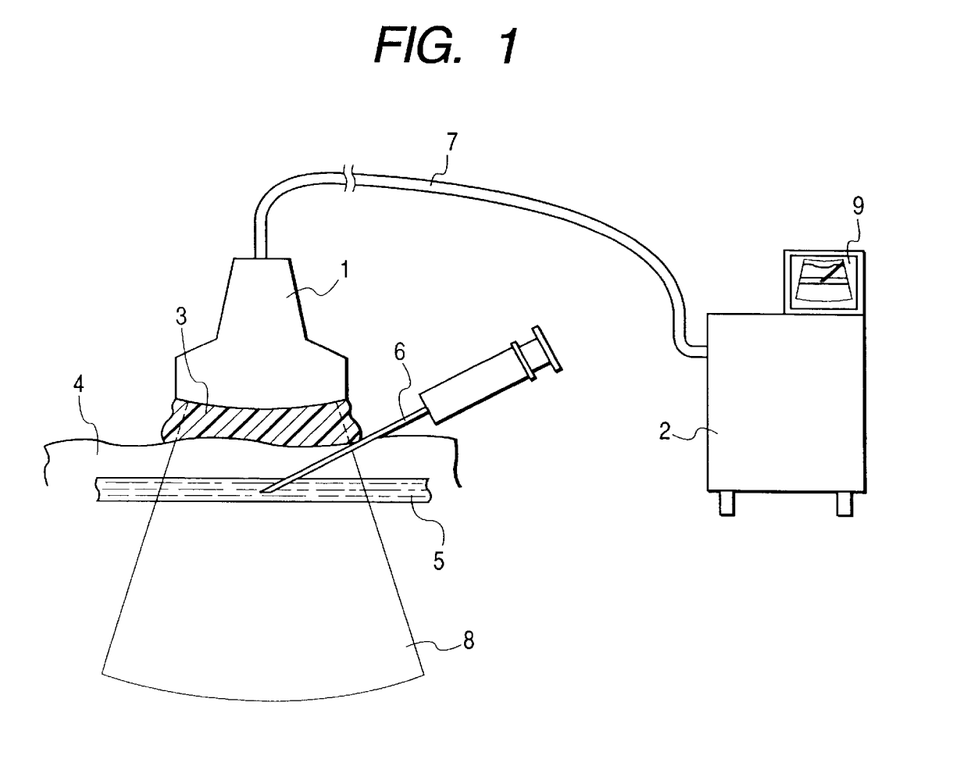
FIG. 1 is a diagram partly in section showing a schematic structure of a blood vessel puncturing device according to a first preferred embodiment of the present invention.

FIG. 1 shows a schematic structure of a blood vessel puncturing device according to the first preferred embodiment of the present invention. In FIG. 1, the device comprises an ultrasound sensor 1. The ultrasound sensor 1 is in the form of an electronic scanning ultrasound probe having a number of ultrasound vibrators (not shown) which are divided into a plurality of groups. The device further comprises a processor 2 having a transmitter section, a receiver section, a signal processor section and a display section 9. The device further comprises an ultrasound propagation medium 3 in the form of gel interposed between the ultrasound sensor 1 and a subject body 4, and a puncturing needle 6 which is stuck into the subject body 4 at an angle of not greater than 30 degrees relative to the subject body 4 along a scanning surface 8 of ultrasound scanning by the ultrasound sensor 1. In FIG. 1, numeral 5 denotes a superficial blood vessel extending in the vicinity of the surface of the subject body 4.

The ultrasound propagation medium 3 is required to have an acoustic impedance approximate to an acoustic impedance (1.5 to 1.65 M rayl) of the subject body 4 and further required to have a small attenuation coefficient and be deformable so as to be easily brought into close or tight contact with the subject body 4 and the ultrasound sensor 1. For satisfying such requirements, it is preferable that the ultrasound propagation medium 3 is made of a material in the form of gel which can be easily deformed, and not made of a solid material. It is preferable that the gel material may be polyurethane gel, silicon gel, polyvinylalcohol gel, polyethylene oxide gel or the like. It is further preferable that the ultrasound propagation medium 3 may be easily attached and detached and of a throwaway type since blood or the like may adhere thereto after the sticking of the puncturing needle 6 into the blood vessel 5, that is, after the use. By interposing the ultrasound propagation medium 3 between the ultrasound sensor 1 and the subject body 4, a high resolution image of the subject body 4 in section near the surface can be obtained.

The puncturing needle 6 is stuck into the blood vessel 5, extending essentially in parallel to the surface of the subject body 4, directly or via the gel ultrasound propagation medium 3 at the angle of not greater than 30 degrees relative to the blood vessel 5. For precisely inserting the puncturing needle 6 into the blood vessel 5 without fail, it is preferable to stick the puncturing needle 6 at a small angle of not greater than 30 degrees relative to the blood vessel 5. A greater angle makes difficult the sticking into a fine blood vessel and requires high-level skill of an operator.

Now, an operation of the blood vessel puncturing device having the foregoing structure will be described.

First, electric signals are transmitted from the transmitter section of the processor 2 via a cable 7 using a plurality of channels so as to be applied to one of the foregoing groups of the ultrasound vibrators in the ultrasound sensor 1. The ultrasound vibrators applied with the electric signals generate ultrasound waves which are then transmitted to the subject body 4 via the ultrasound propagation medium 3. The ultrasound waves received into the subject body 4 are reflected at the boundary between the tissues having mutually different acoustic impedances in the subject body 4, and then received at the ultrasound vibrators of the ultrasound sensor 1. The received ultrasound waves are converted into electric signals at the ultrasound sensor 1, which are then received at the receiver section of the processor 2 via the cable 7. The remaining groups of the ultrasound vibrators are applied with electric signals in a given order using a change-over switch so that the foregoing operations are carried out in sequence. In this fashion, the scanning is performed electronically. The electronic scanning itself is known in the art. The electric signals received at the receiver section are processed at the signal processor section of the processor 2 so that an image in section of the subject body 4 is displayed on the display section 9. In this fashion, the sectional image of the subject body 4 including the blood vessel 5 can be displayed in real time. While watching the displayed image, the operator sticks the puncturing needle 6 into the blood vessel 5 of the subject body 4 at the angle of not greater than 30 degrees relative to the surface of the subject body 4 along the scanning surface 8 so as to carry out blood gathering or medical fluid injection.

In this embodiment, the ultrasound sensor 1 carries out the so-called convex-type scanning. On the other hand, the ultrasound sensor 1 may carry out the so-called sector-type scanning which achieves similar effects. Further, in this embodiment, the electronic scanning is carried out as non-invasive scanning for detecting the blood vessel. On the other hand, ultrasound Doppler signals may be used to detect the blood vessel in a non-invasive manner.

As described above, according to the first preferred embodiment, since the ultrasound propagation medium 3 in the form of gel is interposed between the ultrasound sensor 1 and the subject body 4, the ultrasound sensor 1 can be brought into close or tight contact with the subject body 4 without applying a substantial force. Thus, the deformation of the subject body 4, particularly the blood vessel 5, can be suppressed to be small. Further, since the ultrasound propagation medium 3 in the form of gel is interposed as described above, the subject body 4 near the surface thereof can be displayed distinctly. Accordingly, the operator can stick the puncturing needle 6 into the subject body 4 at the angle of not greater than 30 degrees relative to the subject body 4 while fully observing the superficial blood vessel 5. Hence, the precise needle sticking operation can be achieved for the target blood vessel, particularly even for the fine blood vessel, so that the blood gathering or the medical fluid injection can be carried out easily and safely. This can reduce the burden of the subject body 4 and eliminate the necessity for high-level skill of the operator.

(Second Embodiment)

Figure 2A:
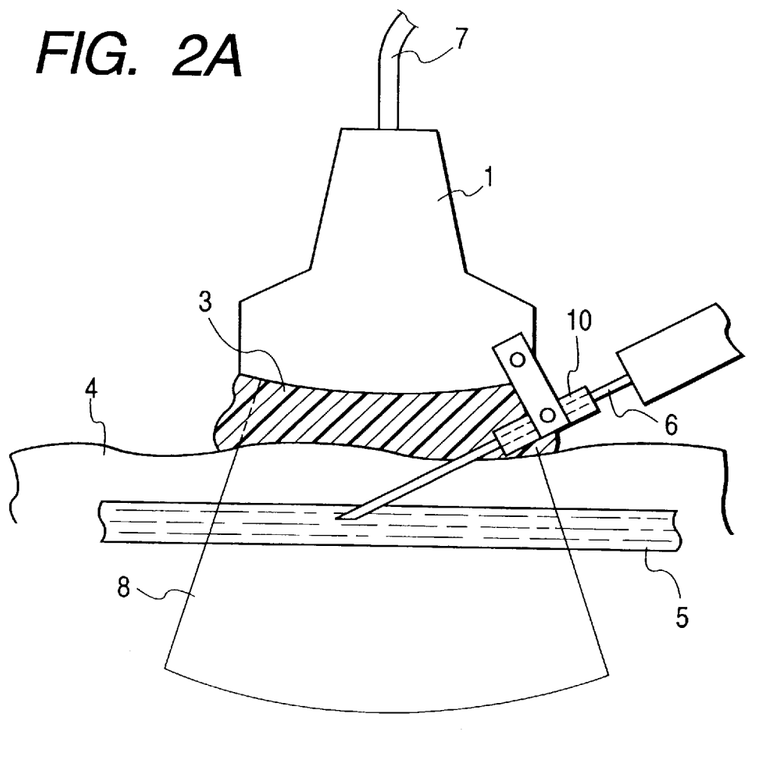
FIGS. 2A and 2B are diagrams partly in section showing a schematic structure of a blood vessel puncturing device according to a second preferred embodiment of the present invention.
Figure 2B:
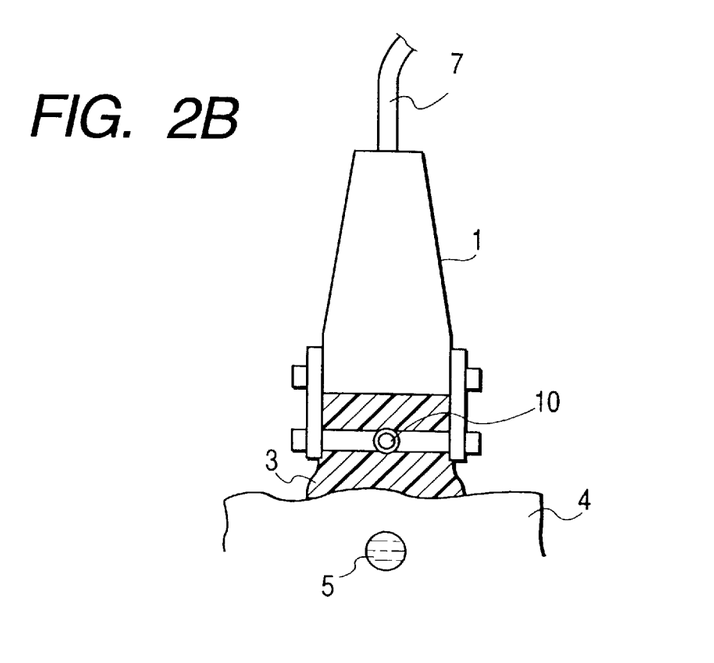

FIGS. 2A and 2B show a schematic structure of a blood vessel puncturing device according to the second preferred embodiment of the present invention. This embodiment differs from the foregoing first preferred embodiment only in that the ultrasound sensor 1 is additionally provided at a housing thereof with a guide member 10 for guiding the puncturing needle 6 so as to be stuck into the subject body 4 at the angle of not greater than 30 degrees.

The guide member 10 is retained by the housing of the ultrasound sensor 1, and a portion of the guide member 10 which the puncturing needle 6 passes through is located in the ultrasound propagation medium 3 and is made of a material which is free of corrosion and can be sterilized, such as metal like stainless steel or plastics.

According to the second preferred embodiment, since the puncturing needle 6 can be stuck into the subject body 4 while being guided by the guide member 10, the sticking of the puncturing needle 6 into the blood vessel 5 can be achieved more precisely at the angle of not greater than 30 degrees while watching the sectional image of the subject body 4.

(Third Embodiment)

Figure 3:
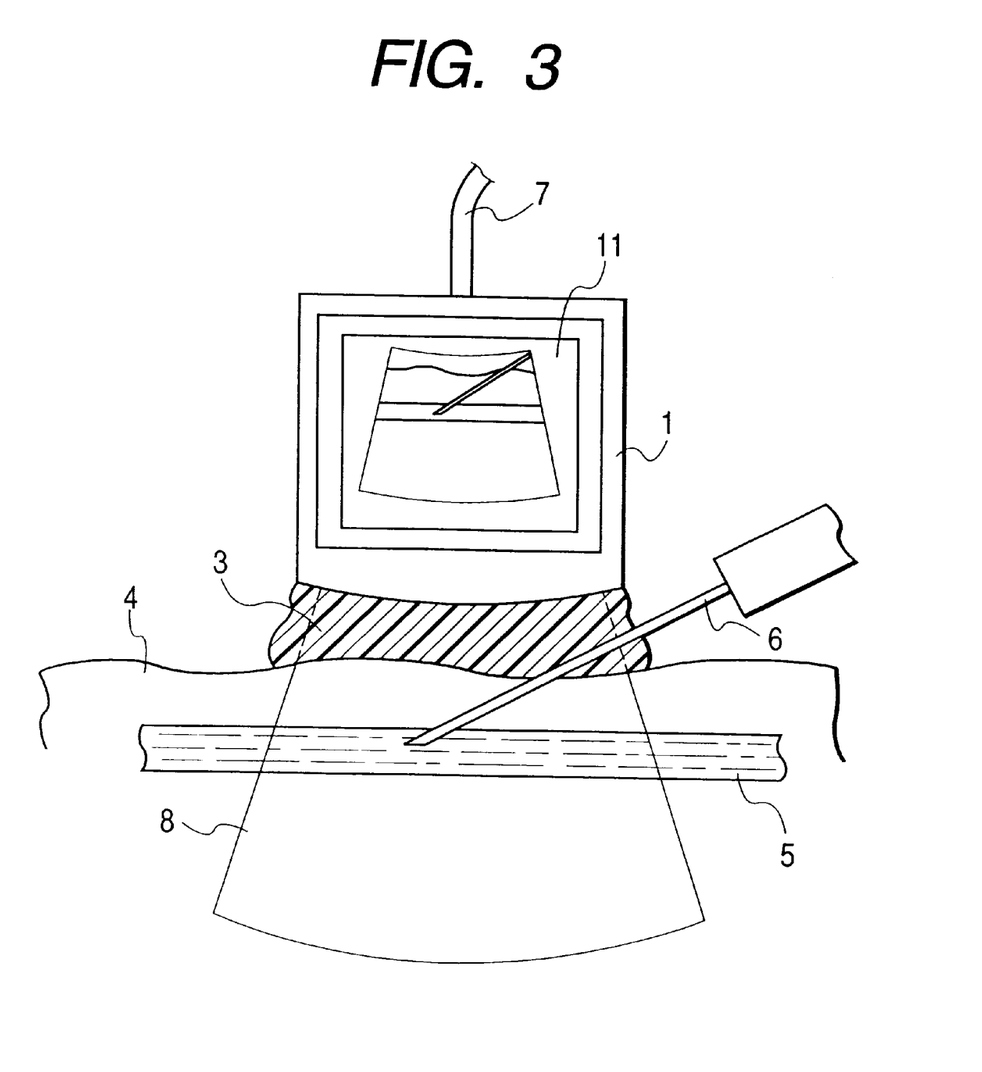
FIG. 3 is a diagram partly in section showing a schematic structure of a blood vessel puncturing device according to a third preferred embodiment of the present invention.

FIG. 3 shows a schematic structure of a blood vessel puncturing device according to the third preferred embodiment of the present invention. This embodiment differs from the foregoing first preferred embodiment only in that an image display monitor 11 is provided, in addition to the display section 9 as shown in FIG. 1, at the housing of the ultrasound sensor 1 so that the sticking of the puncturing needle 6 can be carried out while watching the sectional image of the subject body 4 on the image display monitor 11.

The image display monitor 11 is connected to the display section 9 via the cable 7, and preferably uses liquid crystal or plasma for size reduction.

According to the third preferred embodiment, since the image display monitor 11 is arranged near at hand, the needle sticking operation can be facilitated to accomplish the precise sticking of the puncturing needle 6 into the blood vessel 5.

In this embodiment, the image display monitor 11 is provided at the housing of the ultrasound sensor 1. However, the image display monitor 11 may be provided at a place other than at the housing of the ultrasound sensor 1 as long as it is provided near at hand for the needle sticking operation.

(Fourth Embodiment)

Figure 4:
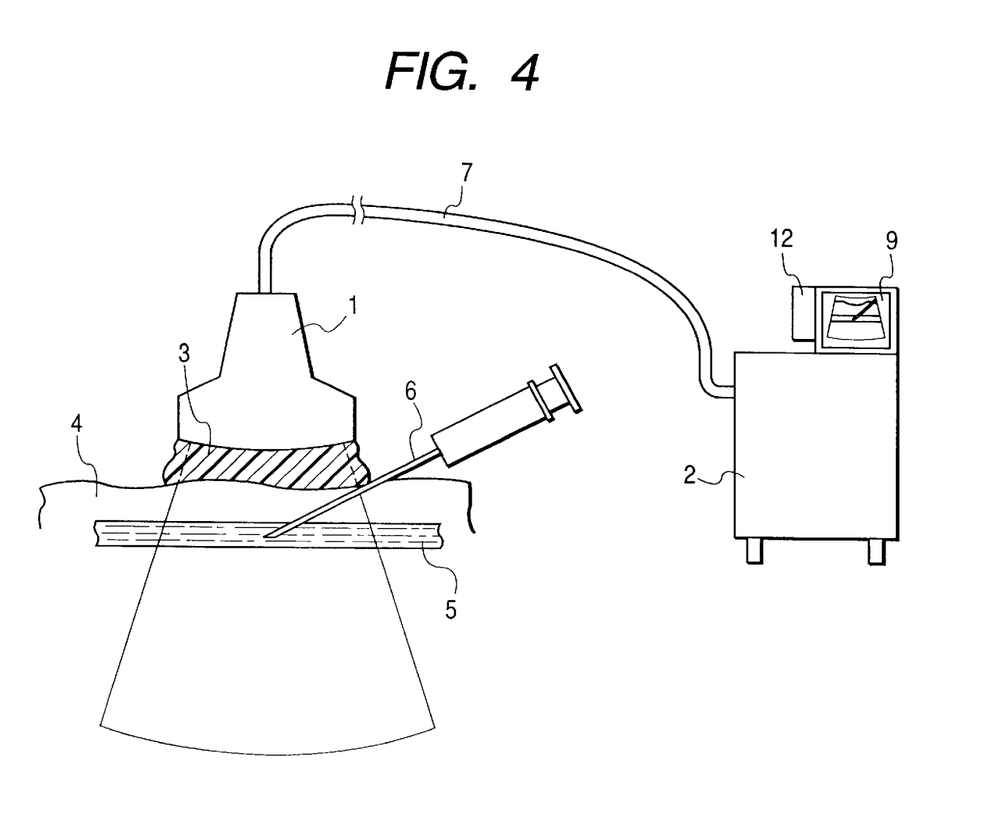
FIG. 4 is a diagram partly in section showing a schematic structure of a blood vessel puncturing device according to a fourth preferred embodiment of the present invention.

FIG. 4 shows a schematic structure of a blood vessel puncturing device according to the fourth preferred embodiment of the present invention. In this embodiment, in addition to the display of the sectional image of the subject body 4, the insertion of the puncturing needle 6 into the blood vessel 5 can be confirmed by audible sounds utilizing ultrasound Doppler signals. The other structure is the same as that of the foregoing first preferred embodiment.

In this embodiment, the sectional image of the subject body 4 is displayed on the display section 9 as in the foregoing first preferred embodiment. While watching the displayed image, an ultrasound pulse Doppler transmit/receive mode can be activated by the operator. Then, by applying a gate on the displayed image, that is, by identifying a portion on the displayed image, where the puncturing needle 6 is to be inserted, the processor 2 controls the ultrasound sensor 1 in the known manner to transmit Doppler signals to the blood vessel 5 at a portion corresponding to the portion identified on the displayed image so as to monitor the blood flow. Reflected signals are received, via the ultrasound sensor 1, at the processor 2 where the received signals are converted into audible sound signals which are then outputted via a loudspeaker 12 as an audible sound.

While monitoring the blood flow by means of the audible sound, the operator sticks the puncturing needle 6, at the angle of not greater than 30 degrees, into the blood vessel 5 at the portion where the gate is applied on the displayed image. When the puncturing needle 6 is actually stuck into such a portion of the blood vessel 5, the blood flow changes due to the presence of the puncturing needle 6 so that the audible sound also changes. Thus, based on the change in sound, the insertion of the puncturing needle 6 into the blood vessel 5 at the target position can be confirmed.

As described above, according to the fourth preferred embodiment, the sectional image of the subject body 4 is displayed on the display section 9 in real time, the blood vessel 5 is located using the ultrasound Doppler signals, the change in blood flow due to the insertion of the puncturing needle 6 into the blood vessel 5 is detected using the ultrasound Doppler signals, and the change in ultrasound Doppler signal due to the change in blood flow is recognized in the form of the change in sound. Thus, the insertion of the puncturing needle 6 can be confirmed by the sounds through ears so that the puncturing needle 6 can be stuck into the target position easily and accurately.

Although the inserting state of the puncturing needle 6 can also be confirmed on the displayed image, it is not so often to only watch the displayed image while inserting the puncturing needle 6 into the subject body 4. Specifically, on many occasions, the insertion of the puncturing needle 6 is carried out through direct observation of the subject body 4 and the puncturing needle 6. Accordingly, by confirming the insertion of the puncturing needle 6 into the blood vessel 5 by the sounds through ears, the needle sticking operation can be performed without moving eyes from the inserting position of the puncturing needle 6, thus resulting in making the needle sticking operation easy and accurate.

In the foregoing fourth preferred embodiment, the ultrasound pulse Doppler method is used. On the other hand, the ultrasound continuous Doppler method may be used to provide similar effects. Further, although the sectional image of the subject body 4 is displayed on the display section 9, a simpler device may be used wherein the sectional image of the subject body 4 is not displayed and only the sound monitoring of the blood flow is carried out.

(Fifth Embodiment)

Figure 5:
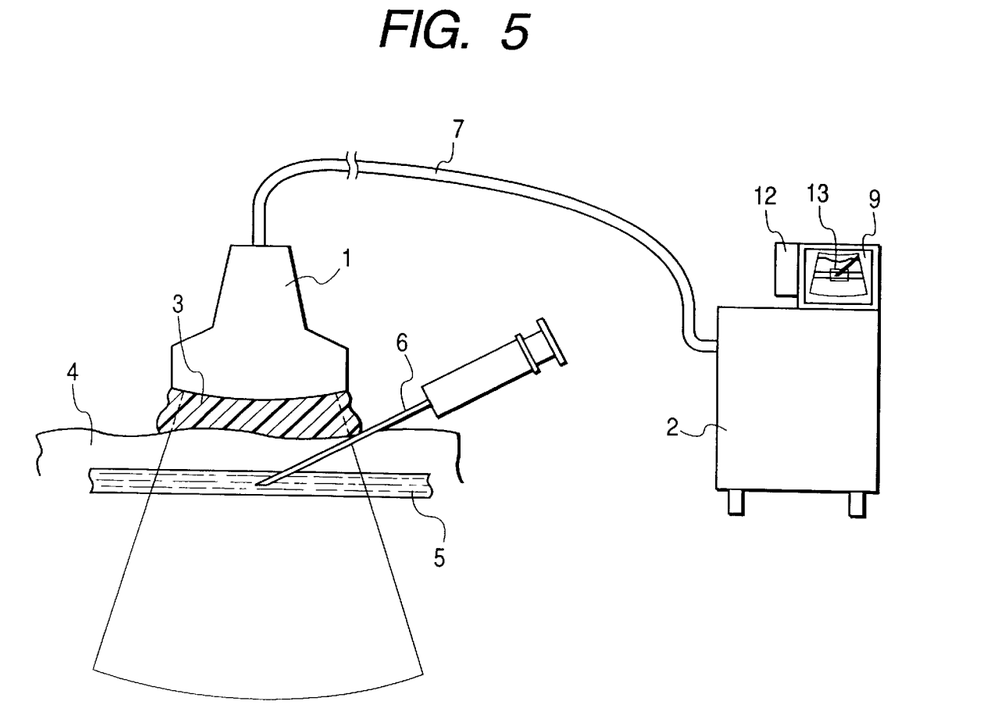
FIG. 5 is a diagram partly in section showing a schematic structure of a blood vessel puncturing device according to a fifth preferred embodiment of the present invention.

FIG. 5 shows a schematic structure of a blood vessel puncturing device according to the fifth preferred embodiment of the present invention. In this embodiment, in addition to the display of the sectional image of the subject body 4, the insertion of the puncturing needle 6 into the blood vessel 5 can be confirmed by generation of a sound or change in sound. The other structure is the same as that of the foregoing first preferred embodiment.

In this embodiment, the sectional image of the subject body 4 is displayed on the display section 9 as in the foregoing first preferred embodiment. While watching the displayed image, a region of the blood vessel 5 where the puncturing needle 6 is to be inserted can be designated by the operator using a marker 13. Depending on the strength of ultrasound reflection signals from the subject body 4, the luminance on the displayed image is changed. Accordingly, in this embodiment, the signal processor section of the processor 2 is controlled to recognize and store the luminance level in the region designated by the marker 13 on the displayed image, and to generate an audible sound signal or change a frequency of an audible sound when the luminance in the designated region changes by more than a given value.

Then, when the puncturing needle 6 is inserted into the designated region of the blood vessel 5, ultrasound reflection signals are generated from the puncturing needle 6 so that the luminance of the designated region is changed. Due to the change in luminance, the processor 2 generates an audible sound signal or changes a frequency of an audible sound, which is outputted through the loudspeaker 12. By means of the sound outputted via the loudspeaker 12, the insertion of the puncturing needle 6 into the target position of the blood vessel 5 can be confirmed.

As described above, according to the fifth preferred embodiment, the sectional image of the subject body 4 is displayed on the display section 9 in real time, the desired region is set on the displayed image, the luminance in the set region is detected, and the change in luminance by more than the given value is outputted in the form of the audible sound. Thus, since the insertion of the puncturing needle 6 into the blood vessel 5 at the target position can be confirmed by the sound through ears while directly observing the insertion of the puncturing needle 6, the puncturing needle 6 can be inserted into the target position of the blood vessel 5 easily and accurately.

While the present invention has been described in terms of the preferred embodiments, the invention is not to be limited thereto, but can be embodied in various ways without departing from the principle of the invention as defined in the appended claims.

What is claimed is:

1. A blood vessel puncturing device comprising:

an ultrasound sensor for transmitting and receiving an ultrasound wave to and from a subject body;

a processor for processing a signal derived from the ultrasound wave received at said ultrasound sensor to display an image of said subject body;

an ultrasound propagation medium in the form of gel interposed between said ultrasound sensor and said subject body;

a puncturing needle which is adapted to be stuck into said subject body at an angle of not greater than 30 degrees relative to said subject body along an ultrasound scanning surface of said ultrasound sensor;

whereby insertion of said puncturing needle into a blood vessel of said subject body can be confirmed on said image.

2. The blood vessel puncturing device according to claim 1, wherein said ultrasound sensor has a housing provided with a guide member for guiding said puncturing needle so as to be stuck at said angle relative to said subject body.

3. The blood vessel puncturing device according to claim 1, wherein an image display monitor is provided near a housing of said ultrasound sensor.

4. The blood vessel puncturing device according to claim 1, wherein said ultrasound sensor carries out one of electronic convex-type scanning and electronic sector-type scanning.

5. A blood vessel puncturing device comprising:

an ultrasound sensor for transmitting and receiving an ultrasound Doppler signal;

a section for locating a blood vessel and detecting insertion of a puncturing needle into said blood vessel as a result of a change in blood flow due to puncturing of said blood vessel which changes said ultrasound Doppler signal received at said ultrasound sensor; and a section for converting the ultrasound Doppler signal received at said ultrasound sensor into an audible sound.

6. The blood vessel puncturing device according to claim 5, wherein said ultrasound sensor is an electronic scanning ultrasound probe.

7. The blood vessel puncturing device according to claim 5, wherein said ultrasound sensor further transmits and receives an ultrasound signal, further comprising a section for displaying an image of said blood vessel based on the ultrasound signal received at said ultrasound sensor.

8. A blood vessel puncturing device comprising:

an ultrasound sensor for transmitting and receiving an ultrasound wave to and from a subject body;

a section for displaying an image of said subject body based on the ultrasound wave received at said ultrasound sensor;

a section for setting a region on said displayed image;

a section for detecting a luminance in said region; and a section for outputting a change of said luminance in the form of an audible sound.

* * * * *